United States Patent
Jacobs et al.

(10) Patent No.: US 7,224,772 B2
(45) Date of Patent: May 29, 2007

(54) RADIOGRAPHY BY SELECTIVE DETECTION OF SCATTER FIELD VELOCITY COMPONENTS

(75) Inventors: Alan M. Jacobs, Gainesville, FL (US); Edward T. Dugan, Gainesville, FL (US); Daniel Shedlock, Gainesville, FL (US)

(73) Assignee: University of Florida Research Foundation, Inc., Gainesville, FL (US)

( * ) Notice: Subject to any disclaimer, the term of this patent is extended or adjusted under 35 U.S.C. 154(b) by 0 days.

(21) Appl. No.: 10/896,243

(22) Filed: Jul. 20, 2004

(65) Prior Publication Data
US 2006/0018434 A1 Jan. 26, 2006

(51) Int. Cl.
G21K 1/04 (2006.01)
G01N 23/20 (2006.01)
G01N 23/201 (2006.01)

(52) U.S. Cl. .................. 378/150; 378/147; 378/70; 378/86

(58) Field of Classification Search .............. 378/6, 378/45, 70, 86, 87, 98.8, 98.9, 146, 147–158; 250/370.09, 505.1, 397
See application file for complete search history.

(56) References Cited

U.S. PATENT DOCUMENTS

| | | | | |
|---|---|---|---|---|
| 3,769,507 A | * | 10/1973 | Kenney et al. | ............... 378/86 |
| 4,825,454 A | * | 4/1989 | Annis et al. | ................... 378/87 |
| 5,260,982 A | | 11/1993 | Fujii et al. | |
| 5,828,720 A | * | 10/1998 | Syrjanen | ..................... 378/38 |
| 6,035,015 A | | 3/2000 | Ruth et al. | |
| 6,122,344 A | * | 9/2000 | Beevor | ........................ 378/88 |
| 6,621,888 B2 | * | 9/2003 | Grodzins et al. | ............. 378/57 |
| 6,711,235 B2 | | 3/2004 | Galish et al. | |
| 6,735,279 B1 | | 5/2004 | Jacobs et al. | |
| 2002/0001366 A1 | * | 1/2002 | Tamura et al. | .............. 378/155 |
| 2003/0136916 A1 | * | 7/2003 | Kearfott et al. | ............. 250/393 |
| 2005/0123089 A1 | * | 6/2005 | Man | ............................... 378/4 |

OTHER PUBLICATIONS

Campbell, J.G., et al., "Detection of Buried Land Mines by Compton Backscatter Imaging", Nucl. Sci. & Engr., vol. 110, pp. 417-424, (1992).
Jacobs, A. et al., "X-Ray Backscatter (Paper II)", Alternatives for Landmine Detection, Research Disclosure, University of Florida, Appendix M. Rand Publishers, pp. 205-223, (2003).

* cited by examiner

*Primary Examiner*—Edward J. Glick
*Assistant Examiner*—Irakli Kiknadze
(74) *Attorney, Agent, or Firm*—Akerman Senterfitt

(57) ABSTRACT

A reconfigurable collimated radiation detector, system and related method includes at least one collimated radiation detector. The detector has an adjustable collimator assembly including at least one feature, such as a fin, optically coupled thereto. Adjustments to the adjustable collimator selects particular directions of travel of scattered radiation emitted from an irradiated object which reach the detector. The collimated detector is preferably a collimated detector array, where the collimators are independently adjustable. The independent motion capability provides the capability to focus the image by selection of the desired scatter field components. When an array of reconfigurable collimated detectors is provided, separate image data can be obtained from each of the detectors and the respective images cross-correlated and combined to form an enhanced image.

13 Claims, 5 Drawing Sheets

RADIOGRAPHY BY SELECTIVE DETECTION OF SCATTER FIELD VELOCITY COMPONENTS

STATEMENT REGARDING FEDERALLY SPONSORED RESEARCH OR DEVELOPMENT

The U.S. Government may have certain rights to the invention pursuant to NASA Contact No. NAS8-6BUY (F0160).

CROSS-REFERENCE TO RELATED APPLICATIONS

Not applicable.

FIELD OF THE INVENTION

The invention relates to radiography, and more particularly to radiography systems which provide selective detection of scatter field components including side scatter, through scatter and backscatter, and methods thereof.

BACKGROUND

In many industrial, military, security or medical applications, images of the internal structure of objects is required. Radiography is often used for imaging. Radiography generally comprises either conventional transmission radiography or backscatter radiography.

When access behind an object to be interrogated is not possible, only backscatter radiography is possible. One method of backscatter imaging is Compton Backscatter Imaging (CBI), which is based on Compton Scattering. Compton Scattering is a phenomenon of elastic scattering of photons by electrons.

Conventional CBI is based on the utilization of single-scatter detected x-rays to form images of the first-scatter spatial distribution and thereby the object internal structure. Higher-order scatter components, which encounter more than one scattering event before emerging from the object being interrogated, are considered to be noise and conventional CBI systems are designed to minimize response to such components. Conventional CBI scanning systems can generally be divided into two classes, which both employ x-ray illumination and utilize a highly-delineated beam:

Class 1. Highly-collimated detectors with field-of-view intersecting the illumination beam at a single object internal "voxel".

Class 2. Uncollimated, large area detectors.

Class 1 devices are extremely inefficient in sensing the scatter field and thus yield extremely slow image acquisition. Such devices can also be insensitive to certain internal detail. Class 2 devices have fast image acquisition, but the unwanted detection of all orders-of-scattering often totally obscures the internal structural detail which is generally desired in the acquired image.

A relatively new type of imaging system based on x-ray Compton backscatter is neither a Class 1 nor a Class 2 system. Lateral migration radiography (LMR) concepts and related systems, were first disclosed in a paper co-authored by one of the inventors of the present invention. (Campbell & Jacobs, Detection of Buried Landmines by Compton Backscatter Imaging, Nucl Sci & Engr, 110, 417, 1992). This configuration proved effective in the detection of buried land mines, including all-plastic land mines.

The LMR system disclosed by Campbell & Jacobs comprised an array of detectors which included both collimated detectors and uncollimated detectors. The collimated detectors disclosed are simple rigid shadow shields. The method disclosed is based on the separation of first scatter detection from the multiple scatter detection by image subtraction methods. Thus, the LMR detectors disclosed by Campbell & Jacobs count either essentially single-scatter (uncollimated) or multiple-scatter photons (collimated) which are slightly influenced by the first scatter distribution. There is no structure or methodology disclosed or suggested for obtaining primarily a given (multiple) scatter component or to eliminate a particular (multiple) scatter component.

SUMMARY

A reconfigurable collimated radiation detector comprises at least one collimated radiation detector. The detector has an adjustable collimator including at least one feature optically coupled thereto, wherein adjustments to the adjustable collimator selects particular directions of travel of scattered radiation emitted from an irradiated object which reach the detector. The collimator preferably includes a plurality of the features and thus multiple apertures.

In one embodiment, the collimator comprises a concave structure including the feature(s) secured thereto disposed on a radiation receiving side of the detector, where the detector is disposed inside said concave structure. In this arrangement, a capping structure is slideably mounted on the concave structure. The concave structure can be a cylindrical collimator. The slideable mount can provide rotation and movement in-and-out of the capping structure relative to the concave structure and result in the feature(s) thus being extended or retracted.

The collimated detector preferably comprises an array of collimated detectors. In this embodiment, at least one collimated detector in the array can detect both selected first scatter photons and selected multiple scatter photons. The detectors in the detector array are preferably each independently adjustable.

A radiography system comprises a source of penetrating radiation for irradiating an object to be interrogated, and at least one reconfigurable collimated radiation detector, the detector having an adjustable collimator including at least one feature optically coupled thereto, wherein adjustments to the adjustable collimator selects particular directions of travel of scattered radiation emitted from the irradiated object which reach the detector. The source of penetrating radiation can be x-ray, gamma ray, neutron or an electron beam source. The source of penetrating radiation can include a modulator for modulating the energy of said penetrating radiation. The collimator can comprise a capping structure including the feature secured thereto disposed on a radiation receiving side of the detector, and a concave structure, the detector disposed in the concave structure. The capping structure is slideably mounted to the concave structure. The slideable mount provides rotation and movement in-and-out of the capping structure relative to the concave structure. The at least one collimated detector preferably comprises an array of collimated detectors.

The source of penetrating radiation and the collimated radiation detector or detector array can be disposed on the same side of the object, or on opposite sides of the object. In another embodiment, the collimated radiation detector is interposed between the object and the source of penetrating radiation, where the radiation detector transmits a portion of penetrating radiation to the object, and a portion of the scattered radiation is detected by the collimated radiation detector.

A method of radiographic imaging includes the steps of receiving a photon flux emerging from an object irradiated with penetrating radiation beam comprising a first scatter component and multiple scatter components at least one reconfigurable collimated detector, selectively detecting portions of the photon flux from the first scatter and multiple scatter photons, the portions being photons having a limited range of trajectories and/or energies, and forming an image, or selected single pixel detector response ratios, from the selectively detected portions. When the at least one collimated detector comprises an array of collimated detectors, the method can further include the step of independently adjusting the collimated detectors in the array. The independent adjusting can take place during the receiving step. The adjustment can be automatic based on feedback of signal-to-noise information. The method can further comprise the step of processing image(s), wherein the processing comprises pattern recognition or neural networks. In another embodiment, the method can include the step of vibrating the object and coordinating movement of the object and the collimated detector or detector array.

The energy of the penetrating radiation beam can be varied during the method. As a result, the image obtained can be a 3D image.

The method can further comprise the step of scanning the object relative to the penetrating radiation beam. In one arrangement, the source of the penetrating radiation beam and the collimated radiation detector are disposed on the same side of the object. In an alternate arrangement, the source of the penetrating radiation and the collimated radiation detector are disposed on opposite sides of the object. in another embodiment, the method can include the step of coordinating movement of the penetrating radiation beam and the collimated detector.

BRIEF DESCRIPTION OF THE DRAWINGS

A fuller understanding of the present invention and the features and benefits thereof will be accomplished upon review of the following detailed description together with the accompanying drawings, in which.

DETAILED DESCRIPTION

Figure 1:
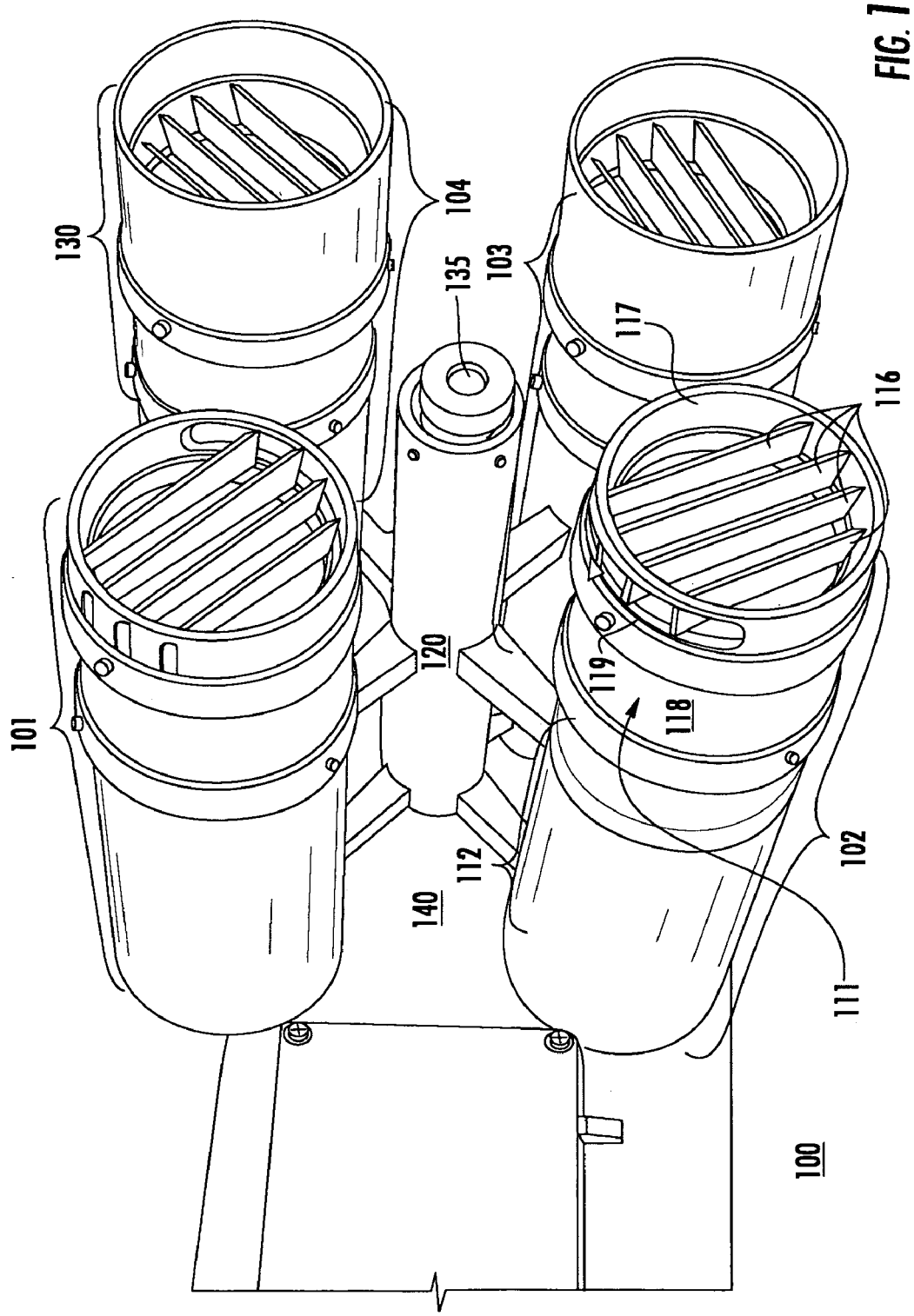
FIG. 1 is a close-up photograph showing the respective collimator assemblies in an exemplary radiography by selective detection (RSD) detector system according to an embodiment of the invention, in various configurations.

Reconfigurable collimated detectors according to the invention emphasize image response to other than simply multiple scatter in objects. Such selective photon detection has been found to significantly increase the contrast and clarity of internal structural details of objects. Moreover, when an array of reconfigurable collimated detectors is provided, a separate image and response can be simultaneously obtained from each of the detectors. In this embodiment, the respective images can be cross-correlated and combined to form an enhanced image of the object. When a detected radiation energy analysis device is provided as described below, optimization of collimator settings and selection of radiation energy limits leads to facilitation of collimator system focusing and enhancement of images.

As used herein, the term "reconfigurable collimated detector" refers to an adjustable collimator which may be moved relative to its associated detector element, such as the detector plane of the detector. An adjustable collimator generally includes features, such as one or more fins, which can be moved relative a detector element. These features are preferably movable relative to one another. Such an arrangement can be contrasted with a conventional rigid and immovable arrangement where the collimator is in a fixed spatial relationship (e.g. angular orientation, distance) with its associated detector element, and the respective components of the collimator (if applicable) have fixed positions relative to one another.

Acquired images using systems according to the invention have shown, under a variety of conditions, that appropriate collimator adjustment and the resulting improved selection of scatter field components leads to a significant improvement in image quality and contrast. The improvement can be so significant, that in some cases objects that are not detectable using conventional CBI systems become readily discernable. Using optional variation of photon energy spectrum detection and illumination described below, further improvements in image contrast and content are possible, including the addition of depth sensitivity and thereby direct 3D-imaging for objects and volumes of interest.

Radiography by selective detection (RSD) systems and related methods described herein, uses the scattering history of the emerging, detected x-ray or other penetrating radiation fields to enhance image contrast of various types of object internal structural detail. Systems according to the invention which have been developed and tested have demonstrated moderately fast image acquisition (for example, 0.05 seconds per pixel for 2 mm to 33 mm pixels) and internal structure image detail not available from either Class 1 or 2 CBI systems for a variety of applications. These applications include land mine detection, flaw and defect detection in aircraft samples, and detection of voids and delaminations in foam thermal insulation.

A reconfigurable collimated radiation detector includes at least one collimated radiation detector. The detector has an adjustable collimator including at least one feature optically coupled thereto, wherein adjustments to the adjustable collimator alters particular directions of travel of scattered radiation emitted from an irradiated object which reach the detector. Such adjustments thus can be used to select directions of travel of scattered radiation which are detected by the detection system and thus form images.

Collimator features can be linear (planar), such as conventional fins, curvilinear having a radius of curvature, or be any type of shadow shield. Although generally formed from a radiation absorbing material, such as lead, collimator features can also be formed from radiation reflective material, such as high density plastic or aluminum. This arrangement is helpful when enhancement rather than removal of certain scatter component(s) is desired.

The collimated detector is preferably part of a collimated detector array comprising a plurality of collimated detectors. The number of collimated detectors in the array can range from 1 to about 100, but generally includes 4 to 10 collimated detectors. The adjustable collimator is optically coupled so that radiation which is passed by the collimator reaches the detector and is thus counted. The collimator is generally, but not necessarily, capable of being physically attached to the detector. As noted above, adjustments to the adjustable collimator relative to the associated detector selects particular directions of travel of incident radiation which are detected by the detector.

A radiation detection system includes a source of penetrating radiation and at least one reconfigurable collimated radiation detector according to the invention. The source of penetrating radiation can comprise an x-ray source, gamma ray source, neutron source or electron beam source. The radiation source illuminates the area to the desired depth to be interrogated. In the case of backscatter radiography, the radiation source is controlled to provide a photon illumination (energy) spectrum with an average optical depth in the object to reach the deepest structure detail desired in the image to be about unity (i.e., one x-ray mean-free-path). In the case of transmission radiography, the radiation source energy is selected to travel through the thickness of the object interrogated, such as at least about 10 MeV for a ⅛ inch thick Fe sheet. The generator voltage is chosen to provide the desired photon illumination (energy) spectrum.

Although generally described herein relative to CBI, the invention is in no way limited CBI. For example, the invention may be applied to any radiography system that can benefit from being able to selectively detect scattered photon object path histories. Accordingly, the invention can yield improved imaging for not only backscatter radiography, but transmission (projection) radiography systems including multiple-view transmission (CT) systems.

The invention is also applicable to hybrid systems including snapshot radiography as described in U.S. Pat. No. 6,735,279 to two of the same inventors as the present application. U.S. Pat. No. 6,735,279 is entitled "Snapshot backscatter radiography system and protocol" and describes an arrangement where the radiation detector is interposed between an object to be interrogated and the radiation source. In this arrangement, the radiation detector transmits a portion of the forward radiation from the radiation source to the object.

FIG. 1 is a photograph of an RSD collimated detector array-based system 100 according to the invention. System 100 includes four (4) collimated detectors 101–104. Collimated detectors 101–104 each include an encapsulated detector 111 having adjustable collimator assemblies 130 optically and physically coupled thereto. For system 100 shown in FIG. 1, the encapsulated detector region begins about 1 inch behind the collimator features 116 when the collimator assembly 130 is fully retracted as described below and extends for about 2 inches in length and terminates in front of encapsulated photomultiplier 112.

Detectors 111 can comprise NaI scintillator crystals operated in the counting mode. Many variations in detector design are possible. This includes using plastic scintillator in place of NaI for higher speed, using an integration mode rather than a pulse mode, variations in the geometry of the detectors, and segmenting the detectors.

Collimator assemblies 130 include outer capping structure 118 disposed on inner collimator tube 117. Inner tube 117 includes four fins 116 (excluding the boundary collimator feature provided by inner tube 117). The four fins 116 in each collimator 130 provide five resulting apertures. Inner tube 117 of collimated detector 102 is in a configuration which exposes its side windows 119, the function of which is explained below.

An x-ray tube (not shown) provides x-rays which emerge from a collimator slit or aperture 135 which is disposed between and essentially equidistant from the four (4) collimated detectors 101–104. Each of the collimated detectors in system 100 and x-ray tube 120 are rigidly held by support plate 140 and related hardware.

The capping structure 118 is slideably mounted and coupled to collimator tube 117 to permit motion in-and-out as well as rotational motion relative to the collimator tube 117 and detector 111. Collimator tube 117 is preferably a Pb lined Al tube, while fins 116 are also preferably made of Pb.

Although collimator assemblies 130 are shown as a cylindrical collimators, the invention is in no way limited. For example, the cross sectional area can be various shapes including elliptical (non-circular), and rectangular (e.g. square).

Although system 100 shown in FIG. 1 includes multiple collimated detectors 101–104 a single reconfigurable collimated detector can be used. However, with a scanner type system it is unlikely to be as effective or efficient as a system with multiple detectors such as system 100. There are situations, however, where a single detector might be practical. For example, in instances when a very small or compact system is of highest priority. In such a situation, a single detector or a single segmented detector might be used.

The collimated detectors 101–104 shown in FIG. 1 are shown as being identical. However, the invention is in no way limited. Depending on the application, it can be advantageous to employ detectors that are not identical in order to do a more effective job of selectively extracting desired velocity/scatter components. Such an arrangement can provide inherent, enhanced detection capabilities for different scatter/velocity components.

Although system 100 is shown having symmetrically positioned collimators 130, the collimators need not be symmetrical. In some applications it may be desirable for them to not be symmetrical for reasons similar to why it may not be desirable to have all detectors identical (or symmetrical).

An important feature of the invention relates to the adjustability of the collimators 130. For example, in applying the invention to the detection of lamination and void defects in low-density materials (e.g. foams) using a multi-fin collimated detector array, a 90 degree rotation of the detector fin plane yielded improved contrast. This collimator orientation enhances the sensing of x-ray lateral migration in a more restricted angle (about 60 degrees of azimuth angle) toward the detectors.

The collimators are preferably independently adjustable. Thus, the fins 116 from one collimated detector 101–104 can be rotated or moved in or out from its respective detector 111 while the other collimated detectors remain fixed. The collimator assemblies 130 shown in FIG. 1 provides independent motion in different directions including rotation, in-and-out movement of capping structure 118 only and in-and-out movement of the collimator assembly 130 as a unit. This independent motion capability provides the capability to "focus" the image by selection of the desired scatter field components. Adjustments to the collimators 130 select particular directions of travel of incident radiation which travel down the Pb lined collimator tube 130 and are detected by the detectors 111.

The collimator assemblies 130 in FIG. 1 are shown in various configurations for the purpose of describing several configurations. The various collimator assemblies are independently adjustable as shown in FIG. 1. Regarding collimated detector 103, collimator 130 is shown having capping structure 118 fully with its fins 116 being perpendicular with respect to x-rays migrating laterally or perpendicularly from the x-ray source beam and recessed. Regarding collimated detector 104, collimator 130 is shown having the capping structure 118 extended, and its fins 116 parallel and recessed. It is noted that the 2 cm extension shown for collimators 130 in collimated detectors 103 and 104 is extended further than generally used to demonstrate the extent of positioning flexibility.

Regarding collimated detector 101, collimator 130 is shown having capping structure 118 fully retracted with its fins 116 parallel (with respect to x-rays migrating laterally or perpendicularly from the x-ray source beam) and extended. Regarding collimated detector 102, collimator 130 is shown having capping structure 118 retracted with its fins 116 parallel and extended. This collimator configuration for collimated detector 102 exposes the windows 119 which allows radiation incident normal or near normal to the entrance of collimated detector 102 to be detected.

The RSD detector array-based system 100 shown in FIG. 1 provides for manual or automatic adjustment of the collimators between scans. Regarding manual adjustments, for exemplary system 100, two methods for focusing are described below. The first method is referred to herein as a coarse focus, while the second method is referred to herein as a fine focus The coarse method, is geometrical in nature, and depends on collimator height, distance between the detector and surface of the object, and the desired scan depth. The second method or fine focus, involves focus refinement to select a portion of the backscatter (or transmission) spectrum, such as a specific energy range of backscattered radiation.

The coarse focus involves determining the distance between the x-ray probe beam and the detector, and the distance between the detector and the surface of the object to be scanned. The approximate depth of the flaw or other feature of interest is also determined. A simple geometry calculation is then performed to determine the length of the collimator. The length should be such that, if a photon penetrates to the desired scanning depth, undergoes a single scattering event, and is reflected back toward the detector, the photon passes near the extended edge of the collimator.

Such focusing removes scatter events that do not penetrate to the desired depth and do not have the desired velocity component. This focusing can also be effectively achieved using suitable geometric positioning of the detector relative to the probe beam and target object even absent a collimator feature.

Coarse focusing could also be performed with a fixed collimator length. The distance between the detector and the surface the object being scanned could be adjusted to meet the requirements as stated above in the coarse focusing. The distance between the x-ray probe beam and the detector could also be varied.

After performing the coarse focus, it may be necessary to select backscattered (or transmitted) photons in a specific energy range or perform fine focusing. Fine focusing usually requires the use of a multi-channel analyzer (MCA) or other suitable device to examine the backscattered or transmitted spectrum. Fine focusing can be performed by either changing the energy of the penetrating radiation source, collimator adjustment, use of a single channel analyzer (SAC), use of a MCA, or any combination thereof. Fine focusing selectively detects photons with a given velocity component in a given energy range that carry the desired characteristic information.

Additional focusing can be performed. The focusing procedure described above is only provided as a starting point to obtain an image. It is likely that many variations of the above procedures apparent to one having ordinary skill can be used to optimize image contrast, acquisition time, or other parameters. For example, the collimator effectiveness could be sacrificed in the interest of decreasing image acquisition time and/or simultaneously acquiring first and multiple-scatter images which are later separated on the basis of energy spectrum analysis. It is also expected that an MCA can be used to determine the detected radiation energy spectrum at a single, central location in an area to be imaged as a guide to remote manipulation of the collimator positions (extension and rotation) for optimizing the coarse focusing procedure.

Although not shown in FIG. 1, adjustment of the collimator assemblies 130 can be made automatic, such as driven by small motors. The automated adjustment could performed either between scans or during scans based on some predetermined optimization criteria.

For example, the optimization criteria could be simply visual, such as based on when an object in an image is seen more clearly. At a higher level, optimization could be based on feedback that uses calculations based on signal-to-noise information, such as increasing the contrast of the desired object to be viewed. Various levels of known image processing routines can be used to increase the contrast and clarity of the image, such as pattern recognition, low pass noise filters, and cross-correlation of different detector array outputs. At a more sophisticated level, neural networks could be employed to provide a database for optimization.

With regard to application to transmission radiography, it is first noted that conventional transmission radiography is (ideally) based on sensing unclouded radiation which passes through the object with no interaction with the object. This is true for both single projection and multiple projection (CT) cases. A conventional "Bucky plate" is generally used to eliminate scattered, penetrating radiation from detection (especially single, 0 to 90 degree scatter). If collimated detectors 130 according to the invention are placed on the penetration-side of the object (i.e., opposite side relative to the illumination), and scanned so that the detector 111 or detector array is fully position coordinated with the illumination beam scan, the system can selectively detect the scattered penetrating radiation field components including both once-scattered and multiple-scattered photons. However, this arrangement requires (in the scanning mode of RSD) a fairly complicated scanning system to coordinate movement of illumination beam and detector assembly, unless the object is sufficiently small in size to allow a yoke connection between source beam and detector assembly.

Contrast in the images of certain classes of object internal structural detail (e.g., lateral delaminations in the space shuttle external tank foam) using transmission radiography according to the invention is enhanced compared to conventional transmission radiography analogous to backscatter radiography described above. Although the usefulness of this mode of imaging has yet to be demonstrated, successes demonstrated for dissection for the backscatter field strongly suggests that some structures invisible to ordinary projection radiography will be imaged using transmission radiography according to the invention.

In the snapshot mode of transmission RSD, the imaging process is no more complex than use of a Bucky plate in conventional projection radiography. As is the case for backscatter RSD, adding radiation energy as an image variable can selectively increase contrast and derivable information in the image, including formation of a 3D imaging.

System 100 was described using scatter field selectivity by restriction of radiation velocity/direction components reaching detectors 111 by collimator assembly 130 orientation manipulation using fixed penetrating radiation energy. However, the radiation energy can be varied to provide added system capability since the detected radiation energy is also an indicator of the interaction path history in the object and, as such, can be restricted to allowed intervals so as to emphasize object internal contrast in acquired images. Moreover, modulation of the illumination radiation energy spectrum coupled with selective detection permits further image contrast control and thereby more information regarding object internal detail from acquired image sets.

As an example, if a set of incident x-ray energy spectra are employed by modulating the x-ray generator through several different kVp energies, such as $E_1$, $E_2$, $E_3$, $E_4$, then designating the corresponding acquired set of backscatter images by $I_1$, $I_2$, $I_3$, and $I_4$, allows for the development of object internal depth description via the systematic subtraction of suitably intensity normalized members of the image set. For example, if $E_4 > E_3$, $E_4$ samples the interrogated object at a depth from the surface greater than $E_3$. Thus, the subtraction image $I_{43} = I_4 - I_3$ represents the object internal distribution within the depth band of the enhanced penetration of the larger energy ($E_4$) over the lower energy ($E_3$).

The same information can be gleaned from the detected energy spectrum using only the single scan at a given $ki_p$, such as $E_4$, if suitable images are generated (say, $i_4$ and $i_3$) which correspond to the principal energy bands used to form $I_4$ and $I_3$. Because the penetrating radiation source generally provides a wide spectrum of energy about a nominal kVp energy, collimators according to the invention can be configured to detect windows, or bands of backscattered or transmitted radiation. Desired energy bands can be determined, for example, by examining detector output signal spectra obtained by using an MCA. Sorting backscattered or transmitted radiation into different energy bins can correspond to use of different kVp energies as described above.

A variety of products can benefit from the invention due to the significantly improved image quality and contrast, improved imaging speed and more compact imaging system as described above. For example, improved scanner systems can be produced which detect flaws and defects in materials and structures, including laminate articles, composites, plastics, insulation and a variety of other low density materials. Scanner devices for security purposes can be used to identify objects hidden in walls, containers and on individuals, as well as portal scanning. Law enforcement and Homeland Security applications include detection of weapons, such as bombs. Some advantages of the invention will be apparent based on the exemplary image data presented below.

EXAMPLES

The present invention is further illustrated by the following specific Examples, which should not be construed as limiting the scope or content of the invention in any way.

An RSD array-based system according to the invention shown in FIG. 1 was used to obtain images of objects inside a gypsum (sheetrock) wall using CBI. The images shown in FIGS. 3 and 4 described below are raw data images without the benefit of filtering or any other image processing.

Figure 2:
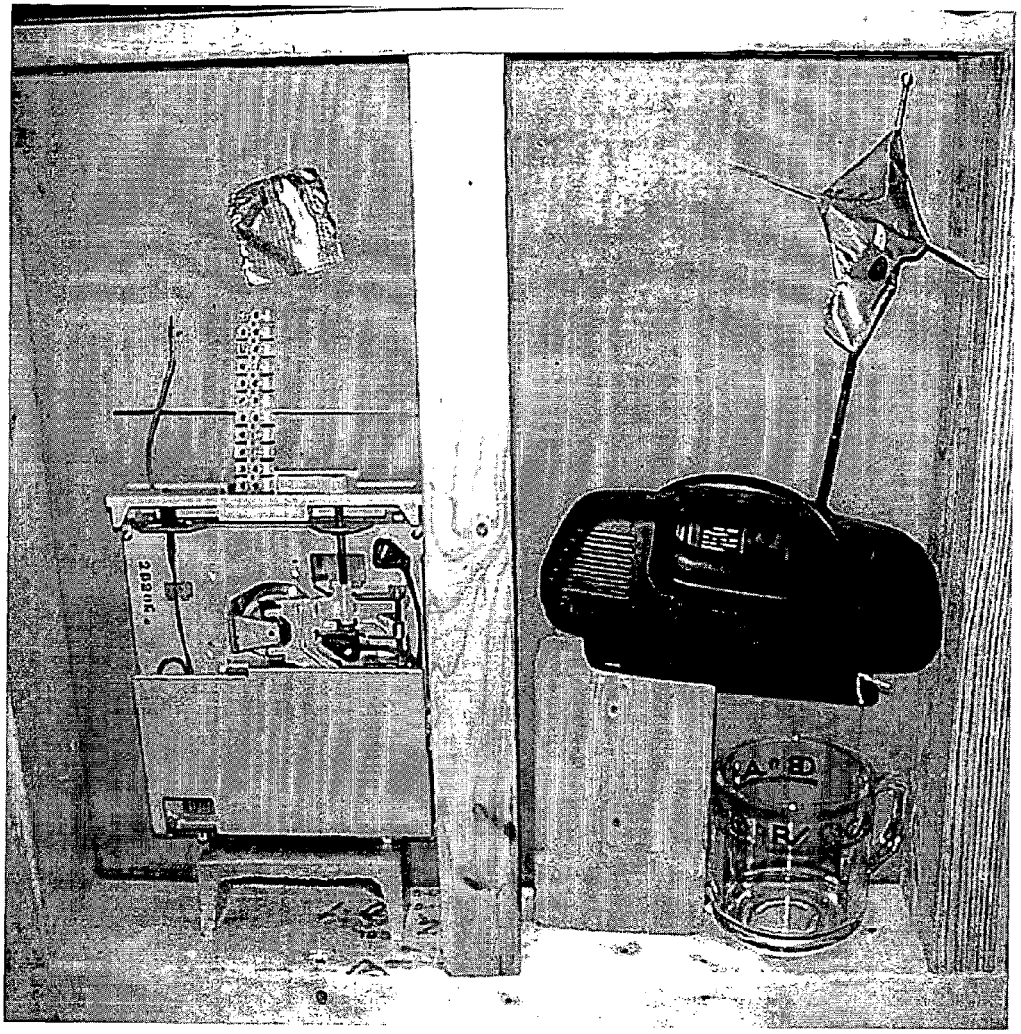
FIG. 2 shows the arrangement of objects as arranged in a wall prior to covering with gypsum for testing with the systems according to the invention.

The wall was of typical construction, framed with 2 inch×4 inch pine-studs. The front of the wall was covered with 3 sheets of 0.5" thick gypsum for a total of 1.5". This arrangement was to simulate commercial construction that uses 2 sheets of ⅝" to meet most fire codes. The following objects were placed inside the wall: 8" wide radio, 5.25" floppy drive, 12 position terminal strip, glass coffee mug, 0.75" diameter circuit chip, ⅛" wide plastic tie, duct tape, a block of wood and an aluminum C-channel. The above items were arranged in the wall as shown in FIG. 2 which was taken before the front wall was covered. The circuit board was duct-taped to the inside surface of the wall. The wall was then scanned with the x-ray backscatter system according to the invention shown in FIG. 1 using 60 kVp x-rays. As shown in FIG. 1, two of the collimated detectors (101 and 102) had collimators oriented parallel and two had collimators oriented perpendicular to the parallel oriented collimators (103 and 104). This arrangement of orientations was found to provide good image contrast or quality.

Figure 3:
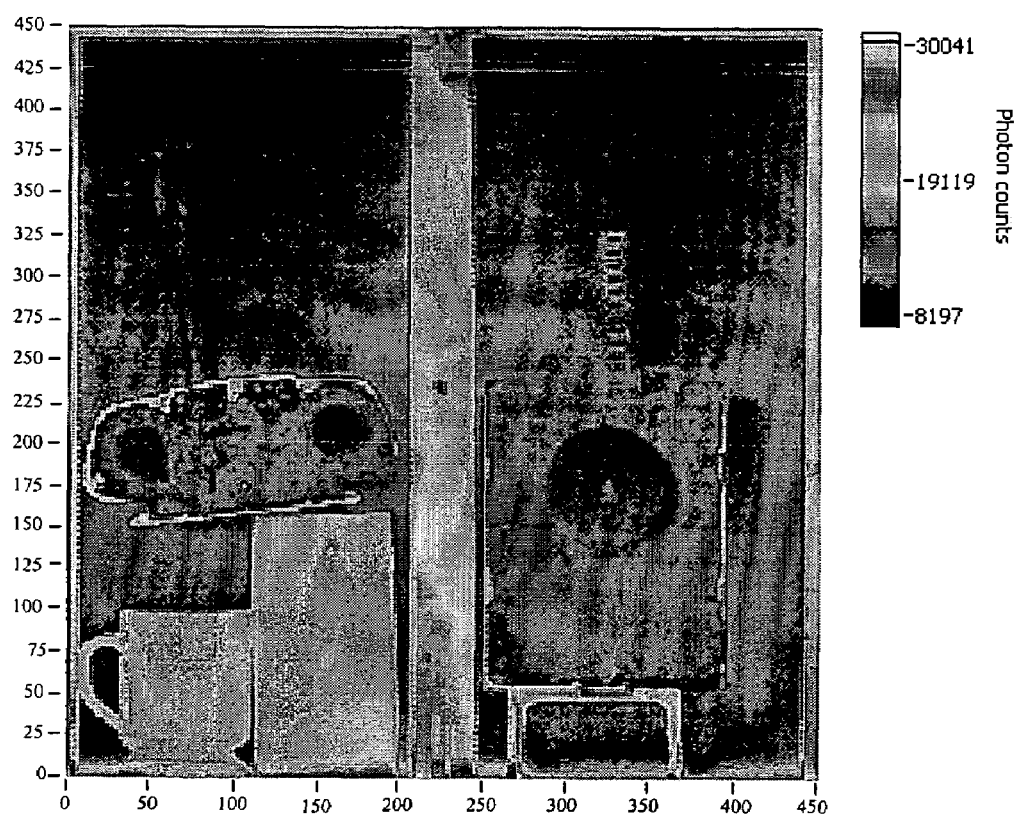
FIG. 3 is an image obtained from an exemplary x-ray backscatter RSD system according to the invention clearly showing images each of the objects shown in FIG. 2 obtained despite the wall being covered by gypsum.
Figure 4:
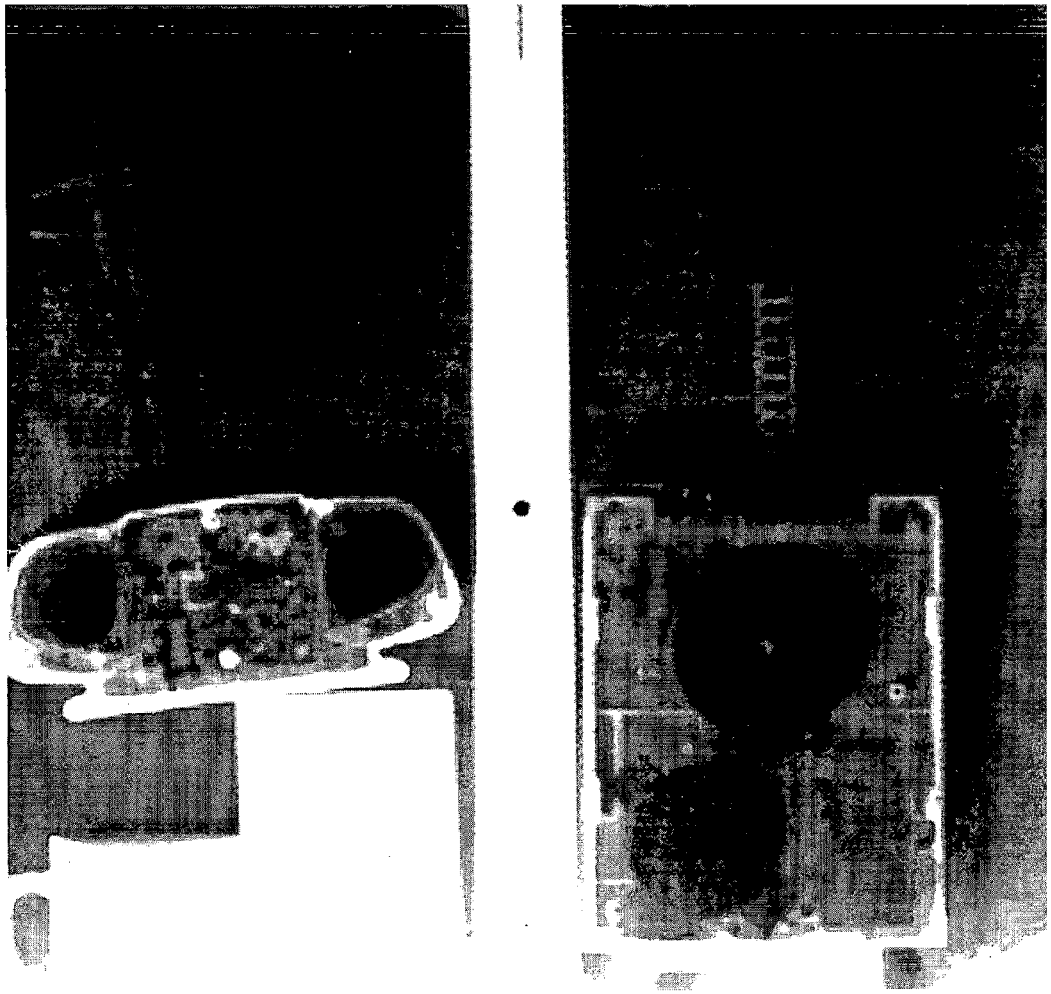
FIG. 4 is a gray scale image of the image shown in FIG. 3 which reveals the electronic structure of a radio and floppy drive through the gypsum.

FIG. 3 shows the RSD image of the wall taken through the gypsum front wall. Each of the objects described above was clearly visible inside the wall on the original color image and are ascertainable of the black and white image provided. The circuit board can be differentiated from defects in the gypsum, because it casts a shadow. The wire sticking out of the floppy, although not directly visible, also casts a shadow as shown in FIG. 3. The plastic tie, which was perpendicular to the terminal strip and above the floppy drive is visible in both FIGS. 3 and 4. Simply changing the image to grey-scale, reveals the electronic structure of the radio and floppy drive as shown in FIG. 4.

Figure 5:
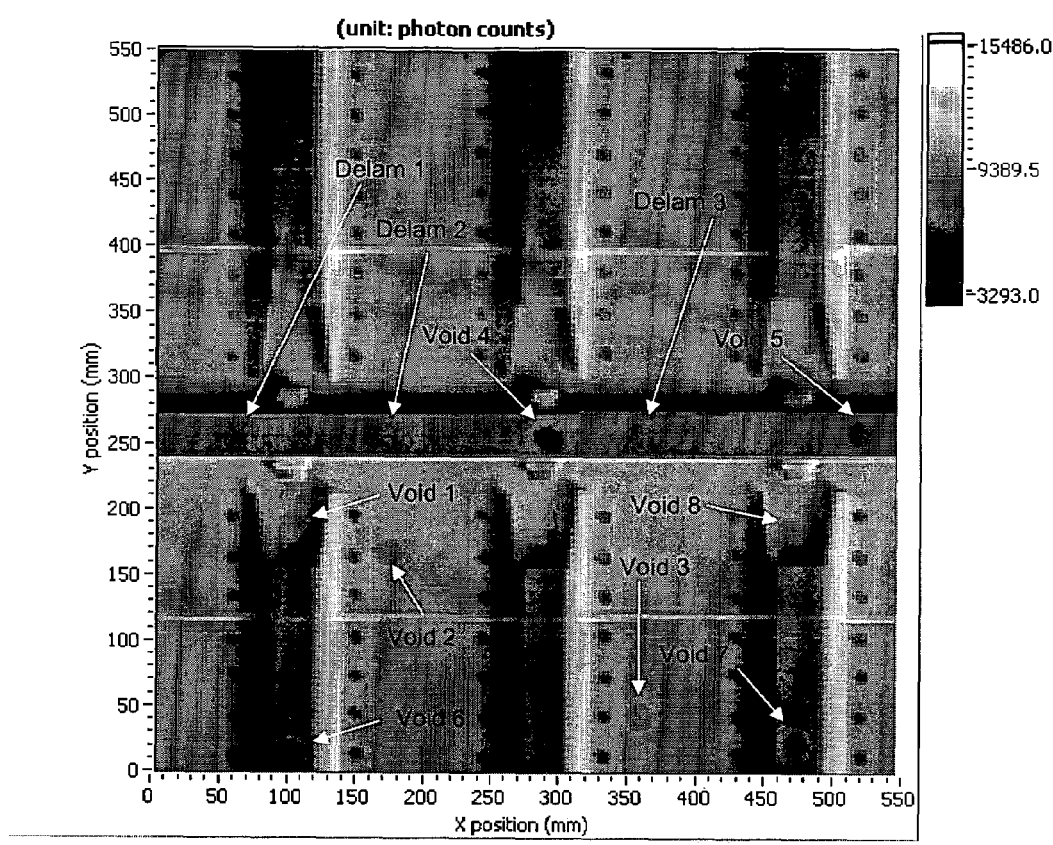
FIG. 5 is an image of a foam test panel obtained from an exemplary x-ray backscatter RSD system according to the invention evidencing a plurality of circular void regions and delaminations in the sample.

FIG. 5 is a grey-scale image from a scan of a foam thermal insulation test panel obtained by one of the detectors shown in FIG. 1. The test panel shown consisted of an aluminum plate onto which the sprayed-on foam insulation (SOFI) is applied. Structural features shown include three vertical metal stringers bolted to the base plate. The stringers are split by a horizontal metal flange centered at about y=260 mm. The bolt heads fastening the stringers to the base plate show up as the dark circles. There are also three large bolts passing through the horizontal metal flange with the bolt head and corresponding nut seen on opposite sides of the flange.

The SOFI was laid down over the base plate and structure with a thickness varying from a few tens of mm up to a few hundred mm. The test panels included voids and simulated delaminations in the SOFI.

At least eight voids are readily apparent in the image shown in FIG. 5. Void 1 occurs at about x=100 mm and y=190 mm at the mouth of the bottom, left stringer. Void 2 occurs to the right of the bottom, left stringer at about x=170 mm and y=170 mm. Void 3 occurs to the right of the bottom, center stringer at about x=360 mm and y=40 mm. Voids 4 and 5 occur on the metal flange; Void 4 is at x=290 mm and y=250 mm and Void 5 is at about x=520 mm and y=260 mm. Void 6 occurs on the top of the bottom, left stringer at x=100 mm and y=10 mm. Void 7 is on the top of the bottom, right stringer at x=475 mm and y=20 mm. Void 8 is at the mouth of the bottom, right stringer at x=470 mm and y=180 mm. The voids have diameters of about 25 mm and a height of the order of 10 mm.

Three simulated delaminations occur on the metal flange at about x=50 mm and y=260 mm (shown as Delam 1), at x=170 mm and y=260 mm (shown as Delam 2) and at x=360 mm and y=260 mm (shown as Delam 3). The delaminations are about 25 mm by 25 mm in cross-sectional area with heights of about 5 to 10 mils. The thin, bright horizontal lines at y=115 mm and y=395 mm correspond to glue lines between different regions of the foam.

It is to be understood that while the invention has been described in conjunction with the preferred specific embodiments thereof, that the foregoing description as well as the examples which follow are intended to illustrate and not limit the scope of the invention. Other aspects, advantages and modifications within the scope of the invention will be apparent to those skilled in the art to which the invention pertains.

We claim:

1. A backscatter radiography system, comprising:
a source of a penetrating radiation beam for irradiating first area of an object to a depth to be interrogated, wherein responsive to said irradiating said object emits backscattered radiation comprising a first backscatter component and plurality of multiple backscatter components, said multiple backscatter components emerging from said object from areas remote from said first area due to lateral migration, and
an array of reconfigurable collimated radiation detectors disposed on the same side of said object as said source of penetrating radiation, a center of at least one of said detectors laterally offset from a line between said radiation beam and said first area of said object, said detectors having adjustable collimators, said collimators comprising:
a concave structure including a plurality of spaced apart features secured thereto, said detector disposed inside said concave structure, and a capping structure, wherein said capping structure is slideably mounted to said concave structure, wherein said collimators select a field-of-view for said backscattered radiation which is less than an entire volume of said object which scatters said beam, but more than a volume which intersects the radiation beam at said first area, and wherein adjustments to said collimators selects particular sets of directions of travel of said multiple backscatter components which reach said detector.

2. The system of claim 1, wherein said, source of penetrating radiation comprises an x-ray, a gamma ray, neutron or an electron beam source.

3. The system of claim 1, wherein said source of penetrating radiation includes a modulator, said modulator modulating the energy of said penetrating radiation.

4. The system of claim 1, wherein at least one collimated detector in said array detects both selected first scatter photons and selected multiple scatter photons.

5. The system of claim 1, wherein said detectors in said detector array are independently adjustable.

6. A method of selective backscatter radiographic imaging, comprising the steps of:
providing an array of collimated radiation detectors having adjustable collimators;
irradiate with a beam of a penetrating radiation a first area of an object to a depth to be interrogated, wherein responsive to said irradiating said object emits backscattered radiation comprising a first backscatter component and plurality of multiple backscatter components, said multiple backscatter components emerging from said object from areas remote from said first area due to lateral migration;
receiving said backscattered radiation, wherein said collimated detectors provide a field-of-view which is less than an entire volume of said object which scatters said beam, but more than a volume which intersects said radiation beam at said first area; wherein selectively detected portions comprising particular sets of directions of travel of said first scatter and said multiple scatter components reach said detectors, and
forming an image from said selectively detected portions.

7. The method of claim 6, further comprising the step of adjusting at least one of said collimators and then repeating said irradiating, said receiving and said forming steps, wherein said adjusting step comprises independently adjusting said collimated detectors in said array.

8. The method of claim 7, wherein said independent adjusting occurs during said receiving step.

9. The method of claim 7, wherein said adjustment is automatic based on feedback of signal-to-noise information.

10. The method of claim 6, further comprising the step of processing said image, wherein said processing comprises using pattern recognition or neural networks.

11. The method of claim 6, wherein an energy of said penetrating radiation beam is varied during said method.

12. The method of claim 11, wherein said image is a 3D imaging.

13. The method of claim 6, further comprising the step of scanning said object relative to said penetrating radiation beam.

* * * * *